US00PP12026P2

(12) United States Plant Patent
Theobald

(10) Patent No.: US PP12,026 P2
(45) Date of Patent: Jul. 31, 2001

(54) SUTERA PLANT NAMED 'NOVASNOW'

(75) Inventor: Hendrik Theobald, Heidesheim (DE)

(73) Assignee: Innovaplant GmbH & Co. KG, Gensingen (DE)

( * ) Notice: Subject to any disclaimer, the term of this patent is extended or adjusted under 35 U.S.C. 154(b) by 0 days.

(21) Appl. No.: 09/545,904

(22) Filed: Apr. 9, 2000

(51) Int. Cl.[7] ..... A01H 5/00
(52) U.S. Cl. ..... Plt./263
(58) Field of Search ..... Plt./263

(56) References Cited

PUBLICATIONS

GTITM UPOVROM Citation for 'Novasnow' as Per Q2 PBR 000205; Mar. 23, 2000.*

* cited by examiner

*Primary Examiner*—Bruce R. Campell
*Assistant Examiner*—Kent L. Bell
(74) *Attorney, Agent, or Firm*—C. A. Whealy

(57) ABSTRACT

A distinct cultivar of Sutera plant named 'Novasnow', characterized by its low-growing and cascading plant habit; very strong plants; vigorous and freely branching growth habit; large dark green leaves; very large white-colored flowers; and long and continuous flowering period.

1 Drawing Sheet

BACKGROUND OF THE INVENTION

The present Invention relates to a new and distinct cultivar of Sutera plant, botanically known as *Sutera cordata*, and hereinafter referred to by the cultivar name 'Novasnow'.

The new Sutera was discovered by the Inventor in October, 1998 in Gensingen, Germany as a naturally-occurring whole plant mutation of the *Sutera cordata* cultivar 'Blizzard', disclosed in U.S. Plant Pat. No. 10,966. Compared to plants of the cultivar 'Blizzard', plants of the new Sutera are stronger, more vigorous, have thicker and stronger stems, have larger and thicker foliage, and have much larger flowers.

Asexual reproduction of the new cultivar by terminal cuttings taken at Gensingen, Germany, has shown that the unique features of this new Sutera are stable and reproduced true to type in successive generations.

SUMMARY OF THE INVENTION

Plants of the cultivar 'Novasnow' have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Novasnow'. These characteristics in combination distinguish 'Novasnow' as a new and distinct cultivar:

1. Low-growing and cascading plant habit.
2. Very strong plants; vigorous.
3. Freely branching.
4. Large dark green leaves.
5. Very large white-colored flowers.
6. Long and continuous flowering period.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new Sutera.

The photograph at the top of the sheet comprises a side perspective view of three typical plants of the new Sutera grown in a 20-cm container.

The photograph at the bottom of the sheet comprises a close-up view of typical leaves and developing flowers of the new Sutera.

DETAILED BOTANICAL DESCRIPTION

In the following description, color references are made to The Royal Horticultural Society Colour Chart except where general terms of ordinary dictionary significance are used. Plants used for the description were grown with three plants per 20-cm container. Plants were grown for about 10 to 12 weeks under full sun and cultural conditions which closely approximate commercial production conditions in Bonsall, Calif. During the production of these plants, day temperatures ranged from about 21 to 35° C. and night temepratures ranged from about 13 to 18° C.

Bontanical classificaton: *Sutera cordata* cultivar 'Novasnow'.

Parentage: Naturally-occurring whole plant mutation of *Sutera cordata* cultivar 'Blizzard', disclosed in U.S. Plant Pat. No. 10,966.

Propagation:

*Type cutting.*—Terminal vegetative cuttings.

*Time to initiate roots, summer.*—About 14 days at 22° C.

*Time to initiate roots, winter.*—About 16 days to 20° C.

*Time to produce rooted cutting, summer.*—About 21 days at 22° C.

*Time to produce a rooted cutting, winter.*—About 25 days at 20° C.

*Root description.*—Fibrous.

Plant description:

*Crop time.*—From rooted liners, about eight weeks are required to produce a fully-grown flowering plant in a 10-cm container.

*Form.*—Mounded; low-growing and trailing. Appropriate for 10-cm and larger containers.

*Branching habit.*—Freely branching with multiple branches and many laterals. Usually about 9 laterals per plant.

*Plant height* (*from soil level to top of plant plane*).—About 9 cm.

*Area of spread.*—About 28 cm.

*Vigor.*—Moderately vigorous.

*Lateral branches.*—Length: Primary laterals: About 24 cm. Secondary laterals: About 9 cm. Diameter: About 2 mm. Internode length: About 2 cm. Texture: Pubescent. Color: 144B.

*Foliage description.*—Leaves simple, generally symmetrical, opposite and long persisting. Quantity per lateral branch: Typically about 24 on primary lateral branches. Length: About 2.25 cm. Width: About 2.5 cm. Shape: Broadly ovate Apex: Broadly acute. Base: Acute. Margin: Dentate to serrate. Texture: Slightly pubescent on both surfaces; somewhat coarse. Color: Young foliage, upper surface: 146A. Young foliage, lower surface: 146B. Mature foliage, upper surface: 147A. Mature foliage, lower surface: 147B. Venation, upper surface: 147B. Venation, lower surface: 147B. Petiole: Length: About 1.1 cm. Diameter: About 1 mm. Color: 147B.

Flower description:

*Flower type and habit.*—Solitary, axillary, salverform flowers; sympetalous; actinomorphic; slender corolla tube abruptly flared and five-lobed. Typically two flowers per node; flowering acropetally. Flowers erect to facing outward at an acute angle. Flowers persistent.

*Flower lastingness.*—Flowers last about five to seven days on the plant depending on temperature and humidity.

*Natural flowering season.*—Continuously flowering under warm growing conditions.

*Quanity.*—Very freely flowering with usually about 100 flower buds and open flowers per plant.

*Fragrance.*—Not detected; leaves, pungent herbaceous fragrance.

*Flower buds.*—Length: About 1.2 cm. Diameter: About 4 mm. Shape: Obovate. Color: 155A.

*Flower size.*—Diameter at lobes: About 1.5 cm. Diameter, corolla tube: About 3 mm. Overall flower height: About 1.4 cm.

*Corolla.*—Petal length (beyond tube): About 6 mm. Petal width: About 5 mm. Petal quantity: Five, fused. Petal shape: Rounded. Petal apex: Rounded. Petal margin: Entire. Texture: smooth. Color: Petal, upper surface, when opening: 155D. Petal, lower surface, when opening: 155D. Petal, upper surface, opened flower: More white than 155D. Petal, lower surface, opened flower: More white than 155D. Corolla throat: 12A to 12B.

*Calyx.*—Appearance: Narrow tube, sepals fused at base. Sepal shape: Narrowly linear, strap-like. Length: About 8 mm. Diameter: About 4 mm. Sepal quantity: Five-parted. Sepal apex: Acute. Sepal margin: Entire. Color: Upper surface: 143B. Lower surface: 143A.

*Peduncle.*—Strength: Delicate, but strong enough to support flowers. Angle: Acute. Length: About 1.2 cm. Color: 144A.

*Reproductive organs.*—Stamens: Stamen number: 4. Anther shape: Reniform. Anther length: About 1 mm. Anther color: 11B. Pollen amount: Scarce. Pollen color: 11A. Pistils: Pistil quantity: One. Pistil length: About 1.2 cm. Stigma shape: Club-shaped, curved. Stigma color: 145A. Style length: About 1 cm. Style color: 145A. Ovary color: 145A.

*Seed.*—Seed production has not been observed.

Disease resistance: Plants of the new Sutera have not been noted to be resistant to pathogens common to Sutera.

It is claimed:

1. A new and distinct cultivar of Sutera plant named 'Novasnow', as illustrated and described.

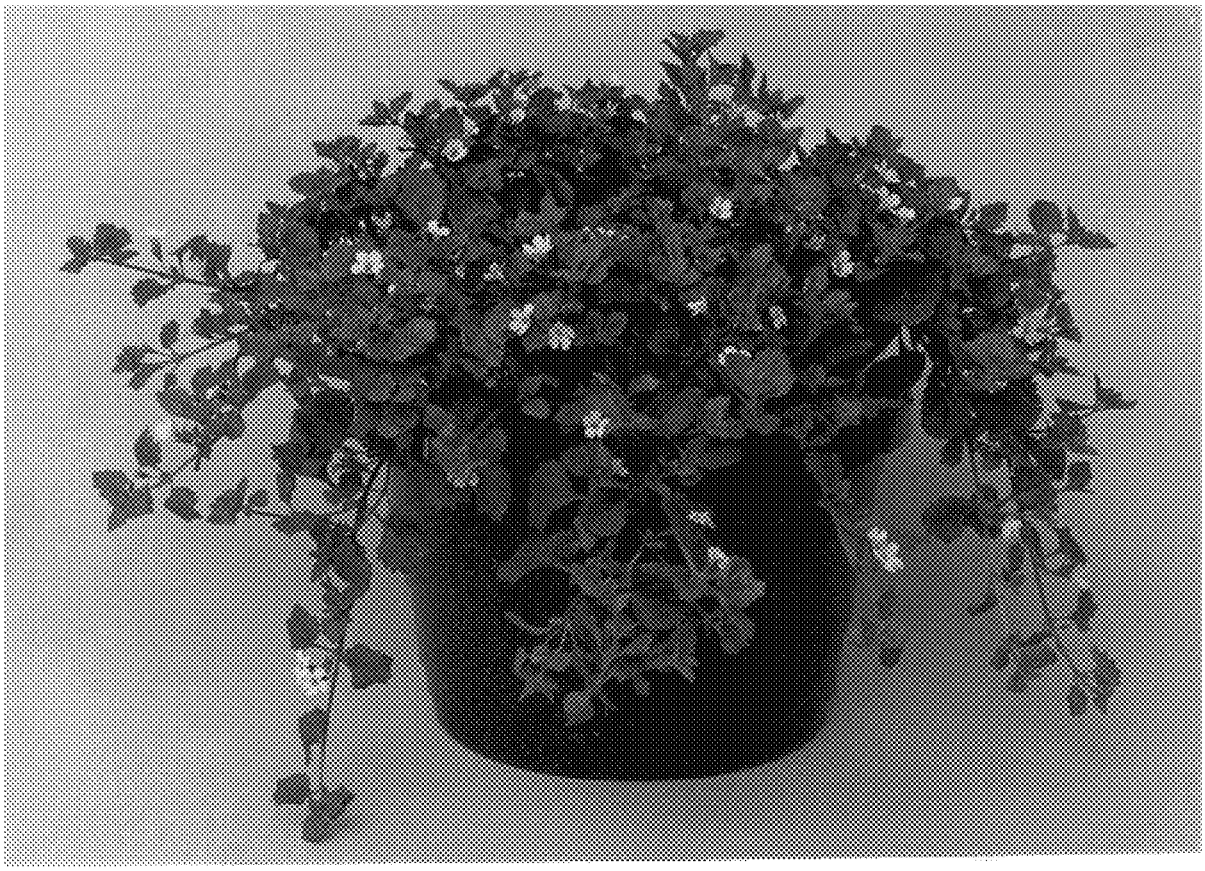
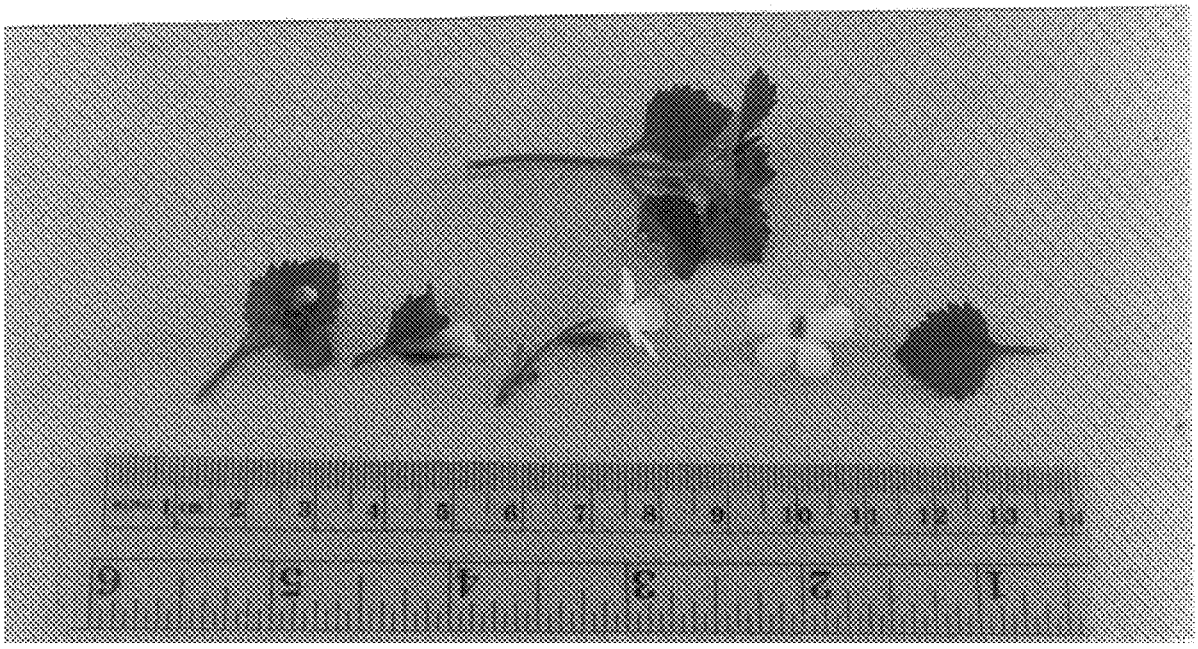

* * * * *